United States Patent
Wolfe et al.

(10) Patent No.: US 6,560,543 B2
(45) Date of Patent: *May 6, 2003

(54) METHOD FOR MONITORING A PUBLIC WATER TREATMENT SYSTEM

(75) Inventors: Thomas D. Wolfe, Rough & Ready, CA (US); James Douglas Elliott, III, Rancho Mirage, CA (US)

(73) Assignee: Perlorica, Inc., Grass Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/055,225

(22) Filed: Oct. 26, 2001

(65) Prior Publication Data

US 2002/0077777 A1 Jun. 20, 2002

Related U.S. Application Data

(63) Continuation-in-part of application No. 09/213,781, filed on Dec. 17, 1998, now Pat. No. 6,332,110.

(51) Int. Cl.$^7$ .......................... B01D 15/00; B04B 13/00
(52) U.S. Cl. .................. 702/22; 702/30; 702/31; 702/188; 210/634; 210/638; 210/660; 210/141; 700/270; 700/271
(58) Field of Search .................. 702/22, 30, 31, 702/188; 210/634, 638, 660, 141; 700/270, 271, 273

(56) References Cited

U.S. PATENT DOCUMENTS

| | | | |
|---|---|---|---|
| 4,830,757 A | 5/1989 | Lynch et al. | |
| 5,492,632 A | 2/1996 | Reber | |
| 5,608,171 A | 3/1997 | Hunter et al. | |
| 5,631,744 A | 5/1997 | Takeuchi et al. | |
| 5,832,410 A | 11/1998 | Lin et al. | |
| 5,835,724 A | 11/1998 | Smith | |
| 5,865,718 A | 2/1999 | Chen | |
| 5,970,426 A | 10/1999 | Mandel et al. | |
| 5,993,662 A | 11/1999 | Garr et al. | |
| 6,023,223 A | 2/2000 | Baxter, Jr. | |
| 6,061,603 A | 5/2000 | Papadopoulos et al. | |
| 6,305,944 B1 | 10/2001 | Henry et al. | |
| 6,317,639 B1 | 11/2001 | Hansen | |
| 6,356,205 B1 | 3/2002 | Salvo et al. | |
| 6,370,448 B1 | 4/2002 | Eryurek | |
| 6,389,331 B1 | 5/2002 | Jensen et al. | |
| 2001/0020195 A1 | 9/2001 | Patel et al. | |
| 2001/0053992 A1 | 12/2001 | Eto et al. | |
| 2002/0023479 A1 | 2/2002 | Burge et al. | |
| 2002/0130069 A1 | 9/2002 | Moskoff | |
| 2002/0133270 A1 | 9/2002 | Hung et al. | |

FOREIGN PATENT DOCUMENTS

WO          WO 01/80494          10/2001

OTHER PUBLICATIONS

Ingo Cyliax, "Remote Internet Data Logging and Sensing", Circuit Cellar Magazine, Embedded PC, PC/104 Quarter 104, Nov. (1997), pp. 53–59.

McKinnon, et al., "Automating Communications with and Developing User Interfaces for Remote Data Acquisition and Analysis Systems", IEEE Transactions on Nuclear Science, vol. 44, No. 3, Jun. (1997), pp. 1062–1064.

(List continued on next page.)

*Primary Examiner*—John Barlow
*Assistant Examiner*—Hien Vo
(74) *Attorney, Agent, or Firm*—McHale & Slavin, P.A.

(57) ABSTRACT

A method of monitoring the daily operating performance parameters for water treatment processes through the collection of localized data. The data is manipulated to generate preconfigured performance, maintenance, and quality assurance reports and further provide automatic submission of data as required for regulatory review of certain water treatment systems such as potable water treatment. The data is collected from sensors located at an equipment site and transferred to a remote computer located by use of the Internet, further all data received and used for generation of reports is also accessible by Internet connection and be delivered directly to the regulatory agency without additional process.

26 Claims, 4 Drawing Sheets

OTHER PUBLICATIONS

Franklin, et al., "Data In Your Face": Push Technology in Perspective, S., SIGMOD Record, vol. 27, Issue 2, Jun. (1998), pp. 516–519.

Soreide, et al., "Mosaic Access to Realtime Data from the TOGA–TAO array of moored buoys", accessed from web site Equatorial Pacific, Oct. 16, 2002, pp. 1–8.

Northwest Fisheries Science Center, National Marine Fisheries Service (NOAA), "Water Recirculation Project", accessed from web site NWFSC:Aquaculture–Water Recirculation Project, Oct. 16, 2002, pp. 1–3.

Northwest Fisheries Science Center, "NWFSC Water Recirculation Project: Data Acquisition and Web Display", accessed from web site NWFSC Web Template, Oct. 16, 2002, pp. 1–3.

Scott, et al., "A Computer Automated Cold Water Recirculating System For Aquaculture Research", accessed from web U.S. Dept. Commerce/NOAA/NMFS/NWFSC, Oct. 16, 2002, pp. 1–9.

Remote Measurement Systems, "Case Studies", accessed from web site Remote Measurement Systems—Case Studies: Fisheries, Oct. 16, 2002, pp. 1–4.

Remote Measurement Systems, "Posting Real–Time Measurement to the Web", Home Energy, accessed from web site Posting Real–Time Measurements to Web Pages, Oct. 16, 2002, pp. 1–5.-

METHOD FOR MONITORING A PUBLIC WATER TREATMENT SYSTEM

RELATED APPLICATION

This Application is a continuation-in-part application to Ser. No. 09/213,781 filed Dec. 17, 1998 now U.S. Pat. No. 6,332,180 the contents of which are incorporated herein by reference.

FIELD OF THE INVENTION

This invention is related to the field of water treatment, and in particular, to a method of monitoring advanced separation and/or ion exchange processes by use of the world wide web allowing review of data collected and complied asynchronously from a web server.

BACKGROUND OF THE INVENTION

Potable water is essential with quality and safety standards regulated by the Environmental Protection Agency (EPA) in accordance with the Public Water System Supervision program. The standards are enforced by local agencies. There are over 170,000 water districts in the United States which provide public drinking water to 90% of Americans.

The EPA has primary standards designed to protect public health against substances that may be harmful to humans if consumed. EPA secondary standards ensure the aesthetic qualities of water such as taste, odor, or clarity. However, each water district remains responsible for monitoring the drinking water itself to ensure that it meets all drinking water standards. The treatment processes for the drinking water must be monitored as well.

In order to comply with the regulatory testing calendar, water districts are required to report a battery of analytical test results varying from hourly to yearly, depending on the source of the water supply. Water systems must monitor their drinking water to ensure that it is safe for their customers. Monitoring schedules differ according to the type of contaminants that may be present in a given water supply. The hourly tests are typically chlorine and turbidity, which can be accomplished with automatic analyzers. Water districts use electronic sensors to monitor the amount of storage, discharge pressure and flow from the systems on a daily basis. Other parameters which are not automatically sensored, but rather are determined by analytical tests, are reported to regulatory agencies on a periodic basis.

Municipal water may be obtained from any source, including seawater, all of which can be made potable by use of proper water treatment equipment. For instance, a reverse osmosis system is capable of lowering the total dissolved solids of sea water to drinking water levels. Despite the sophistication of pretreatment, improper operation can lead to fouled membranes. If fouling occurs but is found quickly, the membranes may be cleaned averting water contamination and associated water treatment repairs. However, if the fouling is not detected quickly, the water treatment system can be irreparably damaged and lead to human health concerns.

One of the problems with maintaining advanced processing equipment is a need for highly qualified individuals. Employment of a full time staff is costly and can be problematic since such monitoring is repetitively and highly qualified individuals can easily become bored. For this reason, all water treatment processes include a large assortment of strategically placed sensors that are typically incorporated into a computer system capable of comparing the sensor values against a pre-set quality level. However, if the operator does not recognize a particular alarm condition, the elaborate array of monitoring equipment is useless.

Municipal water treatment plants are ultimately the responsibility of elected officials. Yet these officials rarely have the technical training or time to allow them directly access the performance parameters of the systems for which they are responsible. The present invention could easily be used to provide a readily understandable presentation of the current performance of municipal water treatment system which was fully accessible by the elected officials as well as plant operators, at any time via the Internet. In addition, in this application of the technology, the same presentation of the system performance could be made accessible to the public at large, allowing interested members of the public to monitor the operation of their own drinking water plants as desired.

Thus, what is lacking in the art, is a means for monitoring water treatment processes in a cost effective manner by highly trained personnel providing regulatory reporting with a real time analysis that can be simultaneously viewed and verified at any time by multiple parties, from any location having access to the Internet.

SUMMARY OF THE INVENTION

The instant invention is a method of monitoring water treatment systems, particularly those subject to regulatory reporting such as potable water treatment systems. The method includes the collection of data which are manipulated to generate preconfigured performance, maintenance, quality assurance, quality control, regulatory, performance graphing, historical trends, and regulatory reports. The data is collected from sensors located at an equipment site and transferred to a remotely located computer by use of the Internet where all data received can be used for the generation of reports also accessible by Internet connection. The reports, graphs and information can be viewed online or downloaded by use of a web browser. Regulatory reports can be forwarded automatically to the regulatory agency via electronic transmission means with the added benefit of receiving reports generated directly from the sensor input thereby eliminated the possibility of human error or tampering. The method allows a single location to monitor countless customers with each customer capable of reviewing information relevant to their equipment, all information is kept confidential by use of appropriate account names, protocols and passwords.

Thus, an objective of the instant invention is to provide a method of compiling information from a plurality of sensors mounted to a water treatment system to generate operational information in near real time, from any location having access to the Internet. The compiled information can be placed into the required format required by regulatory agencies.

Another objective of the instant invention is to provide a system that operates independent of all system controls wherein no feedback is possible to the control system and to transfer such information by a local Internet provider or other internet connection to a consolidating Internet address.

Yet another objective of the instant invention is to provide an Internet report system that can be viewed online or offline providing alarms by the use of current and historical records.

Still another objective of the instant invention is to provide automatic polling of sensor data, automatic transmission of sensor data, data to graph conversion, data to statistical report conversation, compliance calendars, e-mail notification of compliance and the ability to automatically file data and reports with the regulatory agency.

Yet another objective of the instant invention is to provide scheduled and predicted maintenance reports by the use of the current and historical records; providing emergency notification of failures, shutdowns, critical parameters, membrane damage by the use of electronic mail, pager, and/or human voice calling.

Another objective of the instant invention is to regulatory reporting without the need for human interface thereby negating human error or tapering.

Still another objective of the instant invention is to provide a method of regulatory reporting which is independent and/or complimentary of the existing monitoring system.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
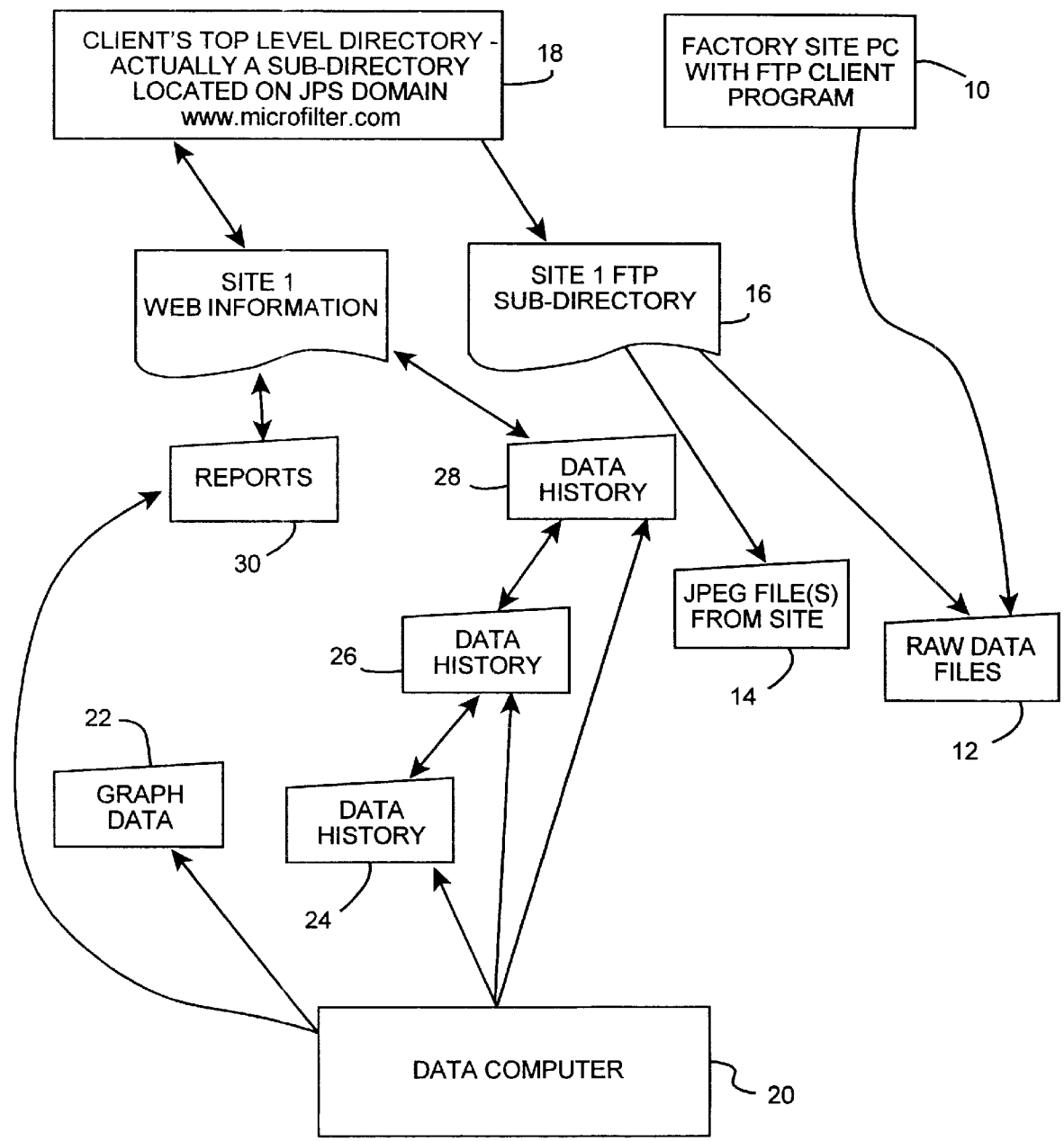
FIG. 1 is a pictorial representation of the various modules that make up the instant invention.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

The instant invention is a monitoring system that incorporates the use of the Internet for providing a remote location for assimilation and dissemination of configured reports regarding water treatment systems primarily for the purpose of preparing and submitting regulatory reports required for operation of certain water treatment systems. Data is first collected by the use of sensors and on-line analytical devices from numerous locations on a water treatment system. For instance, a typical potable water treatment system may include sensors for, but not limited to: raw water temperature, conductivity, pH, chlorine level, fluoride, turbidity, conductivity; and so forth. The data generated by the sensors are forwarded to a data capture module or programmable controller 10 which performs the required analog to digital conversion for use in transmitting data files 12 and 14 to a main server located off-site by use of local Internet access. The data capture module can be composed of readily available commercial devices, such as Analog to Digital boards, specifically designed for the purpose of converting instrument readings or data to computer readable form. Data files may also be transferred by modem to a processing site via direct dial up to the central server, or via well known methods such as RPC or FTP. The local data capture module, or programmable controller 10, continuously scans sensor data inputs and automatically logs and archives operating data at specified intervals. System operation for real time monitoring 16 by accessing an Internet web site 18 specifically set up for a particular customer. The data is also manipulated by the data computer 20 with ftp uploads wherein operating parameters are displayed graphically in a tabular format which are color coded to provide an indication of normal operation, warning status or alarm conditions. The information from the sensors are used for determining critical information for the proper evaluation of the water treatment system which is normalized and graphically displayed for performance evaluation, preventative maintenance, scheduling, or for trouble shooting.

Historical performance data 24 can be plotted and presented also in geographical 26 or tabular form 28 for selected periods. This provides for not only a historical analysis of system performance, but also a record of prior performance for quality control or regulatory recording purposes. In this manner, the software is designed to continuously scan sensor input and compare the current value with alarm set points in a pre-determined report 30. These set points may be different than actual locally set alarm points. For example, management may wish to see all instances where conditions were close to an alarm or trigger point and such conditions may be summarized in exception reports. The device further has the ability to notify authorized users by e-mail or use of a pager when process conditions meet or exceed, or appear likely to exceed, normal alarm conditions. This provides a layer of redundancy in system operation, and allows non technical and management personnel to be notified promptly in the event of non standard operations.

The system will automatically prepare the documentation required to meet the regulatory requirements. The documentation can be printed out and mailed or transmitted by facsimile to the regulatory agency. Ideally the regulatory report document is sent directly to the regulatory agency via electronic transmission methods using .ftp (file transfer protocol) or e-mail (smpt) thereby eliminating the opportunity for human error and/or manipulation. The customer is capable of accessing data related to his processing equipment including all data, information and reports by use of any computer having Internet access capability. This eliminates the need for specialized equipment and allows a manager operating at his desk to access the data from any location whether it be the office, home, or on the road without the use of specialized computer systems. The software program continually updates the reports for the customer or a customer may view the reports or download them from the web site.

In the preferred embodiment, the reports are configured to each regulatory requirements when a service agreement is established. For instance, the process system operations would contain the information necessary to monitor, maintain, supervise and trouble shoot process plant system performance. In this manner the typical information and parameters process block would include, if applicable, flow rates, pressures, differential pressures, permeate quality, pH, alarm conditions, tank levels, and a graphical presentation of applicable process performance parameters and trends. A regulatory report would contain the information necessary to enable a regulatory agency to determine operational parameters including quality and quantity of the treated water to confirm compliance with specifications and standards. Information in this report would typically include treated water production rate (flow), treated water consumption rate (flow), treated water storage volume, reserve capacity (at current production and consumption rates), final treated water quality, reports and archive data for regulatory compliance and/or QA/QC documentation.

Calculated/estimated overall plant efficiency may be provided as a percent of theoretical efficiency. Efficiency could be based on the theoretical minimum water, power, and chemical consumption versus actual consumption calculated.

Figure 2:
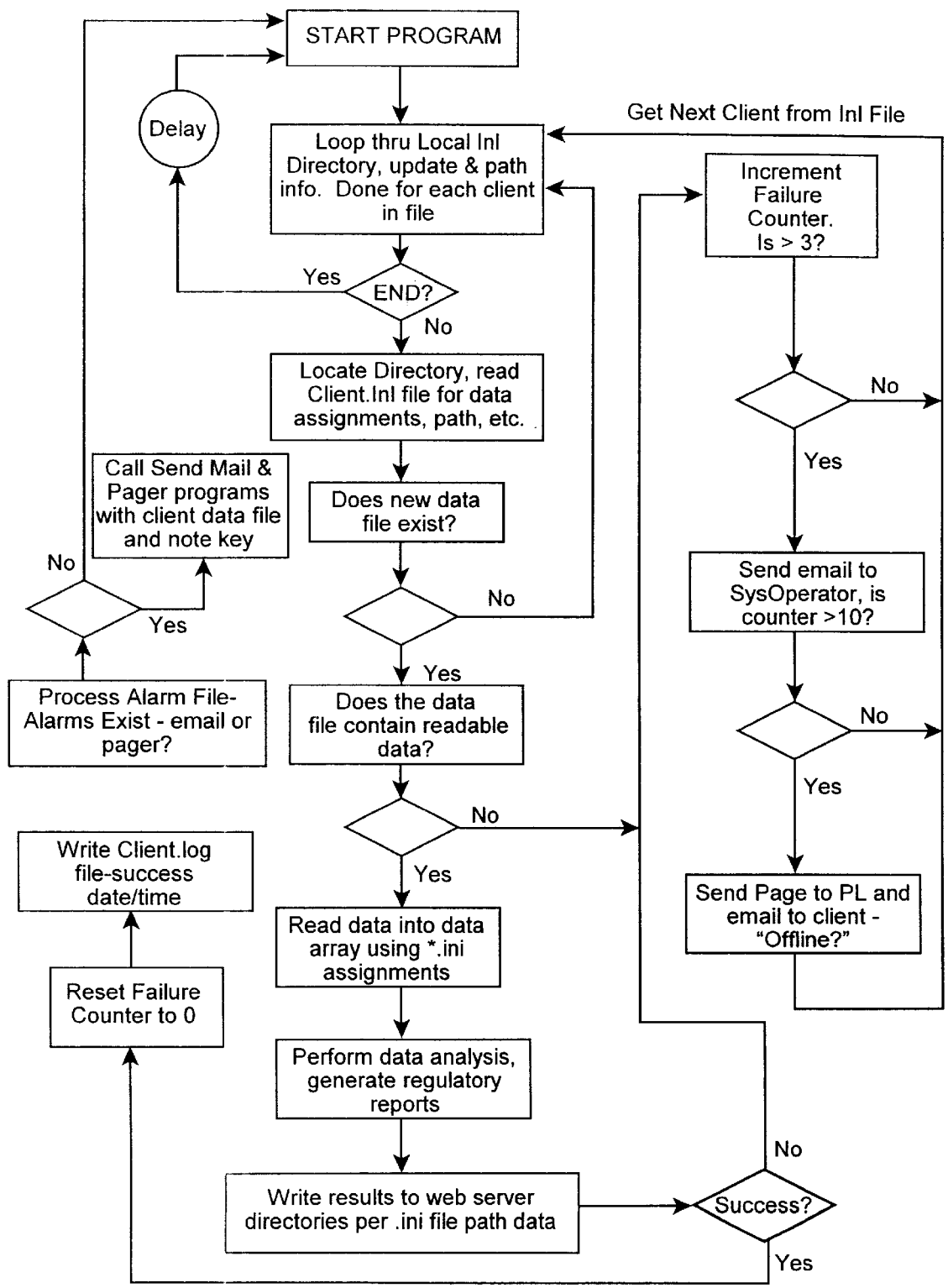
FIG. 2 is a flow diagram of the start-up operations of the software.
Figure 3:
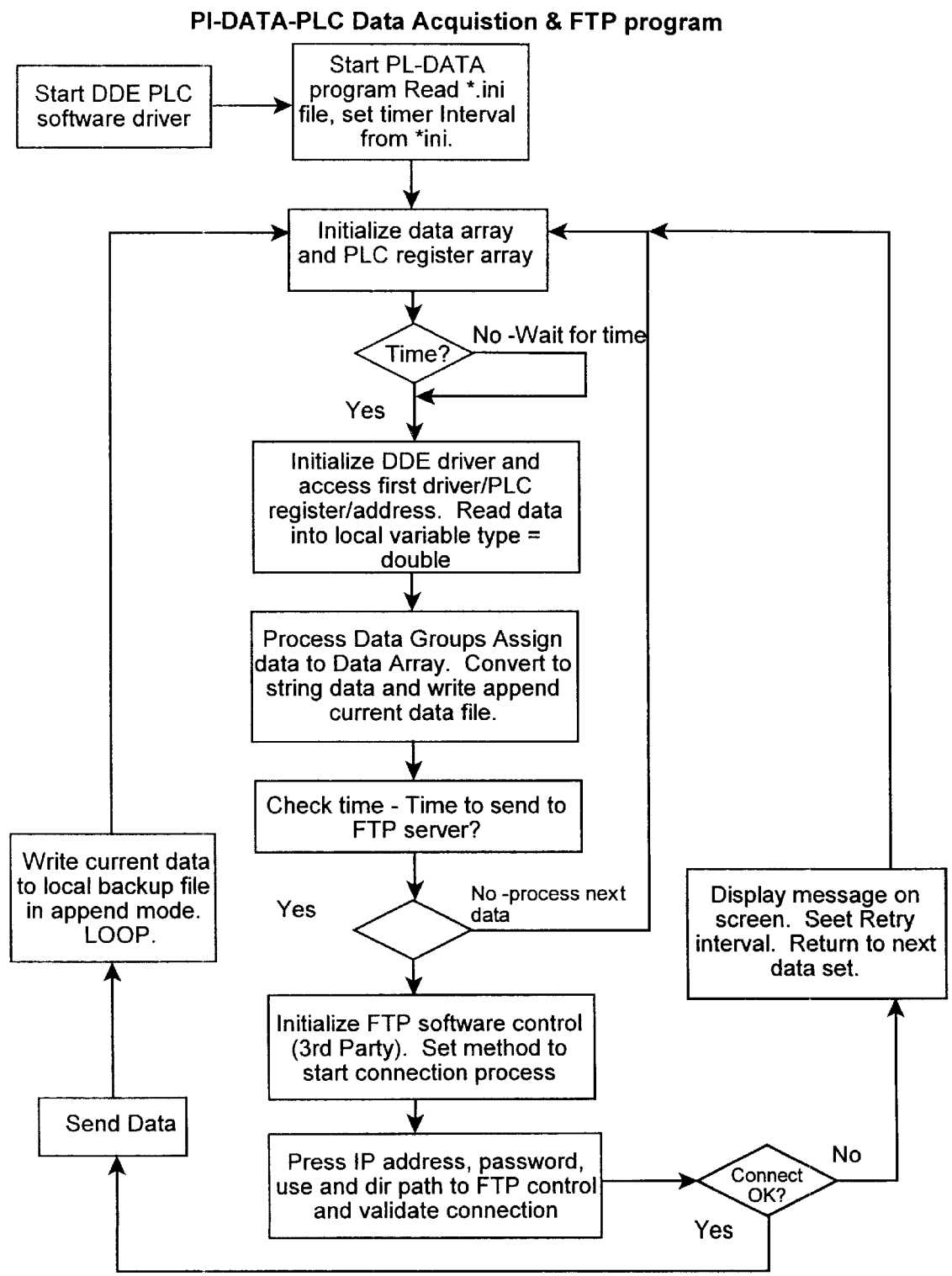
FIG. 3 is a flow diagram of the data acquisition operations of the software.
Figure 4:
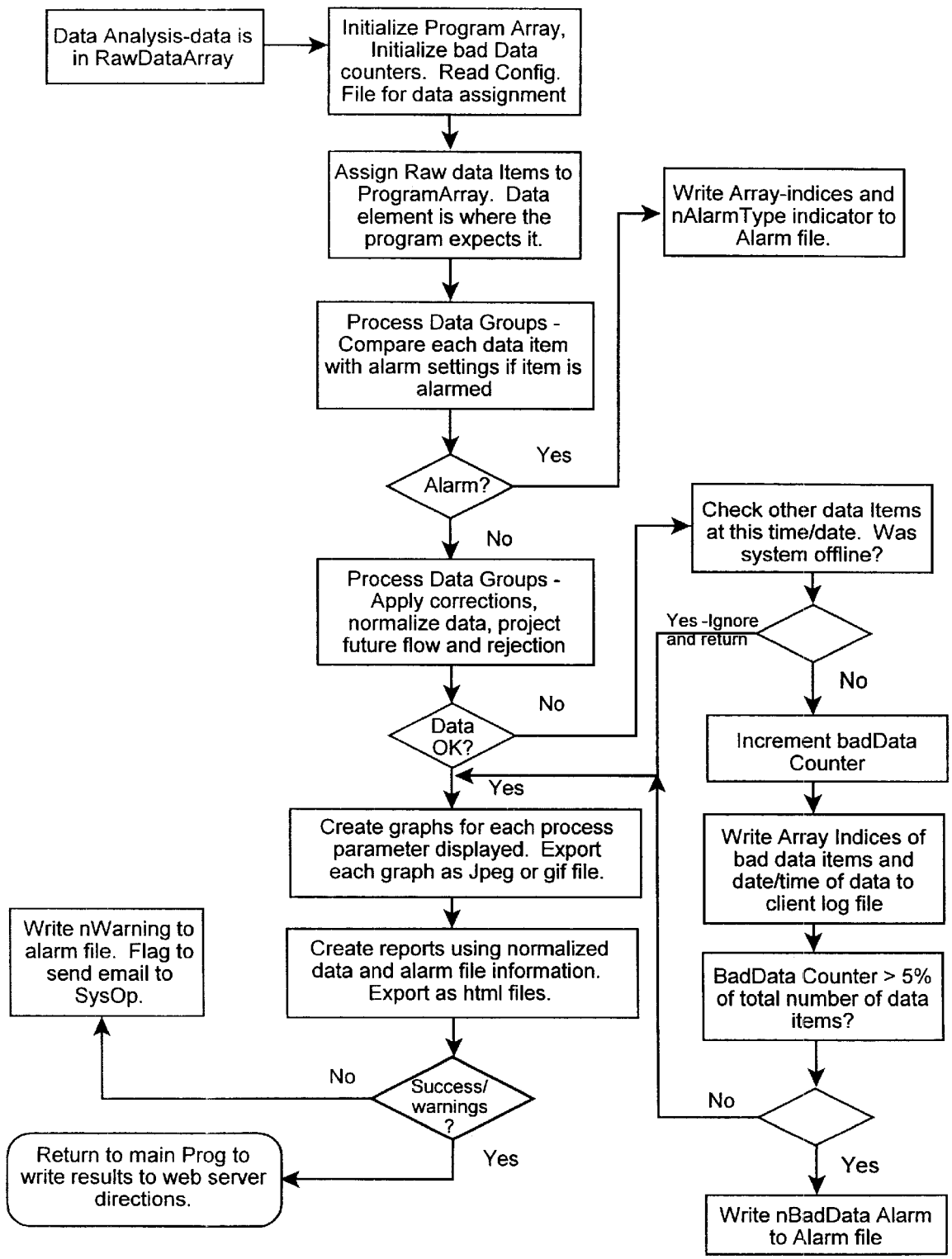
FIG. 4 is a flow diagram of the data analysis and report generator of the software.

Now referring to FIGS. 2–4, set forth is the operation of the program. This program has four essential parts—the local data capture means, the data sending means, the data computation and analysis, and the web server.

At the local site, where the process equipment is located, a communications interface is used with a local computer to capture data from the process instruments through the analog to digital convertor or output of the Programmable Logic Controller (PLC). If a PLC is used, a software driver specifically designed for the process PLC is utilized for this application. These drivers are available commercially and with the correct driver and some slight modification nearly every commercial PLC can be accessed. This local computer is connected to the Internet either via dial up access or through a dedicated network connection.

A local configuration file on the local computer tells the program which PLC register addresses to access, any scaling factor which needs to be applied, a physical description of the data being collected for example—temperature or pressure, and how often the access is required. The local configuration file can be updated from the primary server if necessary during a communication session with the server or via a modem connection, thus eliminating the need to travel to the site to maintain the software. The data set collected is then converted to a comma delimited string value and stored locally on the hard disk in a sequential file. This file may also be encrypted by software if necessary. Other local file storage methods are obvious to those skilled in the art.

At set intervals, usually in the order of 1–30 minutes, the local program calls a third party control software module (the data sending module) which activates the Internet connection software. Either a third party Internet Service Provider (ISP) is accessed via dial up connection and a modem or a local network is used. The contents of the local data file are then sent via ftp protocol, or via a direct connection to the remote database using technology such as ADO, or via e-mail (smtp) to either an ftp server which can be accessed by the main data computer or directly to the main data computer. The local computer uses the access path and passwords stored on its hard disk in the configuration file to determine where to send the data. If the configuration file has changed since the last update, this file is also sent.

The local computer program then transfers the contents of the data file to a historical data file on the hard disk providing an on site data backup source. The current data file is then reused for storing new data. Typically the amount of data transferred each cycle to the ftp server or data computer is relatively small—several kilobytes—so that the load on the network is minimal. It will also be apparent to anyone skilled in the art of programming that this local computer, if so desired, could also be used to access the Internet and the results of main data computation could be displayed locally.

Main Computer

At the main data computer, the high level program also utilizes a series of configuration parameters, which may be stored in "*.ini" type files or a database to establish the path to where the raw data exists. This data is the data which needs to be analyzed, formatted and presented. The configuration file also contains the output path names to the various directories used by each client when they access their data via a web browser.

The main program loops through each data set in turn, restarting as needed. Data is either accessed from the main computer's hard disk or downloaded from the ftp server. The configuration file allows the main program to determine which data point is which part of a typical reverse osmosis, ion exchange system or other water treatment process. The configuration file also holds information on which units the local process collects data. For example, the configuration file may indicate that at site B, the third data item in each data set is the applied feed pressure expressed in kilopascals. The program must display a consistent set of units and thus translates all pressure values into the common format of pounds per square inch (psi) using a units conversion subprogram. Furthermore, in this example, the feed pressure is critical in determining the future and current performance of the system in reference to its performance when new. Furthermore, for reverse osmosis membranes, changes in pressure are related to age, production rate, and temperature and vice versa. Thus a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. The instant invention does this automatically and reports normalized data to the output.

Of course, many more process parameters are monitored, normalized, and analyzed by the computer software of this invention.

The results of these analyses are then utilized in the following manner:

Raw performance data compared to normalized or corrected data is plotted in simple, easy to understand graphs which are published in the jpeg, gif, or other format readily usable by a web browser.

The performance is compared to predicted normal performance and if the differential exceeds preset limits (found in the configuration files) selected individuals are automatically sent E-mail or in more extreme cases a pager or fax (paper) alert.

Process and regulatory reports are prepared from the data and published as html tables for access by a web browser.

Historical data is regularly updated and new graphs are prepared, in the jpeg or gif format as noted.

Scheduled maintenance requirements are reviewed by the software and if needed within a preset time—usually within one week, or E-mail notification is sent to the designated individual(s).

In either case, the output is sent to the designated web directories on a web server attached to the Internet. These directories are appropriately protected for access only by authorized individuals. It may be appreciated that the physical location of the Main Data Computer, the ftp server, and the web server may be at the same location or remote from each other. In addition mirror sites can be maintained as necessary to provide reliable service.

The main computer may be either a stand alone unit or can serve as the Internet web server in itself in addition to performing the actual computations. No particular operating system is preferred for the web server and either Microsoft Windows or UNIX may be utilized depending on convenience, reliability, and cost issues.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A method for remote monitoring the daily operating performance parameters for a water treatment system employing an electronic control system comprising the steps of:
   a) accessing raw operating data from said electronic control system;
   b) providing a storage means on a local computer for storing said raw operating data in an electronic format;
   c) coupling said local computer to an Internet server computer;
   d) transmitting said stored raw data using transmission methods to a remotely located Internet server computer;
   e) storing said transmitted raw data on said Internet server computer;
   f) accessing such data asynchronously from said Internet server computer;
   g) manipulating said tansmitted and stored raw data into an analysis result and a report result; and
   h) uploading said analysis result and said report result to an Internet web server in a format suitable for access and visualization with a web browser computer program.

2. The method of claim 1, further including the step of filing said report result with an appropriate regulatory agency.

3. The method of claim 1, further including the step of transmitting said report result directly to an appropriate regulatory agency using electronic transmission means.

4. The method of claim 3, wherein said electronic transmission means is via e-mail.

5. The method of claim 3, wherein said electronic transmission means is via ftp (file transfer protocol).

6. The method of claim 3, wherein said electronic transmission means is via direct connection over the internet to a database located on a remote computer.

7. The method of claim 1, wherein said step of manipulating said transmitted and stored raw data includes routines to notify selected individuals on the basis of the stored parameters relating to the performance of the system being analyzed.

8. The method of claim 1, wherein said step of manipulating said raw data includes routines to notify selected individuals on the basis of said selected parameters relating to compliance testing dates and performance criteria.

9. The method of claim 1, wherein said step of accessing said raw operating data from said electronic control system includes the steps of reading, querying, and storing data accessed from said electronic system by use of a communications card interface.

10. The method of claim 1, wherein said steps of accessing said raw data, storing said raw data locally, and transmitting said raw data to said remotely located internet server computer is integrated into said electronic control system.

11. The method of claim 1, wherein said water treatment system produces potable water.

12. The method of claim 1, wherein said water treatment system includes secondary and/or tertiary treatment.

13. The method of claim 1, wherein said electronic control system is defined as a programmable logic controller (PLC).

14. The method of claim 1, wherein said step of accessing raw operating data from said electronic control system includes a serial interface coupled to said local computer, whereby said serial interface is operable to transfer serial output of raw operating data from said electronic control system to said local computer.

15. The method of claim 1, wherein said step of accessing raw operating data from said electronic control system includes a USB interface card coupled to said local computer, whereby said USB enabled interface is operable to transfer output of raw operating data from said electronic control system to said local computer.

16. The method of claim 15, wherein said local computer includes software program operable to perform the steps of reading, querying, and storing data accessed from said electronic control system.

17. The method of claim 1, wherein said digital data files are transmitted to said Internet server computer by .ftp.

18. The method of claim 1, wherein said digital data files are transmitted to said Internet server by e-mail.

19. The method of claim 1, wherein said digital data files are transmitted to said Internet service via direct connection over said internet to a database located on a remote computer.

20. The method of claim 1, further including the steps of:
   I) comparing said analysis result with known optimum performance parameters;
   j) determining differentials between said known optimum performance parameters and the analysis result; and
   k) sending notifications to pre-determined recipients if known limits for said differentials are exceeded.

21. The method of claim 1, further including the steps of:
   I) comparing said analysis result with known Federal and State EPA parameters;
   j) determining differentials between said known Federal and State EPA parameters and the analysis result; and
   k) sending notifications to pre-determined recipients if known limits for differentials are exceeded.

22. The method of claim 1, further including the steps of:
   I) comparing said report result with know Federal and State EPA parameters;
   j) determining the differential between said known Federal and State parameters and the report result; and
   k) sending notifications to pre-determined recipients if known limits for said differentials are exceeded.

23. The method of claim 16, wherein said software program utilizes mathematical normalization and prediction routines to produce said analysis result.

24. The method of claim 1, further including the steps of converting said transmitted and stored raw operating data into visual graphs.

25. The method of claim 1, further including the steps of converting said transmitted and stored raw operating data into statistical reports.

26. The method of claim 1, further including the steps of converting said transmitted and stored raw operating data into a compliance calendar.

* * * * *